(12) United States Patent
Szeles et al.

(10) Patent No.: US 8,128,911 B2
(45) Date of Patent: *Mar. 6, 2012

(54) ANTIBACTERIAL DENTIFRICE EXHIBITING ENHANCED ANTIPLAQUE AND BREATH FRESHENING PROPERTIES

(75) Inventors: Lori H. Szeles, Howell, NJ (US); Xiaoyan Liu, Highland Park, NJ (US); Malcolm Williams, Piscataway, NJ (US); M. Teresa R. Carale, Princeton, NJ (US); Michael Prencipe, Princeton Junction, NJ (US); James G. Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 272 days.

This patent is subject to a terminal disclaimer.

(21) Appl. No.: 10/143,388

(22) Filed: May 10, 2002

(65) Prior Publication Data

US 2003/0211053 A1 Nov. 13, 2003

(51) Int. Cl.
*A61K 8/66* (2006.01)
*A61K 8/96* (2006.01)
*A61Q 11/00* (2006.01)

(52) U.S. Cl. ............... 424/50; 424/49; 424/51; 424/52; 424/53; 424/54; 424/56; 424/57; 424/58

(58) Field of Classification Search ............. 424/94.1, 424/94.2, 49–58
See application file for complete search history.

(56) References Cited

U.S. PATENT DOCUMENTS

| 4,042,679 A * | 8/1977 | Gaffar .................. 424/54 |
| 4,058,595 A | 11/1977 | Colodney |
| 4,152,418 A | 5/1979 | Pader .................. 424/50 |
| 4,823,803 A * | 4/1989 | Nakamura ............... 600/530 |
| 5,158,763 A | 10/1992 | Gaffar et al. |
| 5,431,903 A | 7/1995 | Majeti et al. |
| 5,616,314 A | 4/1997 | Gallopo et al. |
| 5,624,906 A * | 4/1997 | Vermeer ................ 514/23 |
| 5,869,618 A * | 2/1999 | Lippman et al. ......... 530/387.1 |
| 6,379,654 B1 * | 4/2002 | Gebreselassie et al. ...... 424/50 |
| 6,616,916 B1 * | 9/2003 | Karpe et al. ............. 424/49 |

FOREIGN PATENT DOCUMENTS

| CA | 1322726 | 10/1993 |
| FR | 2051992 | 4/1971 |
| RU | 2152778 | 7/2000 |
| RU | 2171781 | 8/2001 |
| WO | 9629978 | 10/1996 |
| WO | WO02/34213 A2 | 5/2002 |

OTHER PUBLICATIONS

Balls et al., 1937, "The Milk-Clotting Action of Papain," J. Biological Chemistry 121(2):737-745.
Gaylord et al., eds., 1963, "Antiseptics and Disinfectants," Kirk-Othmer Encyclopedia of Chemical Technology, 2nd ed., vol. 2, pp. 632-635.
International Search Report in International Application No. PCT/US03/14569 mailed Aug. 12, 2003 and Written Opinion in International Application No. PCT/US03/14569 mailed May 19, 2004.

* cited by examiner

*Primary Examiner* — Jeffrey S. Lundgren
*Assistant Examiner* — Savitha Rao
(74) *Attorney, Agent, or Firm* — Nikhil A. Heble

(57) ABSTRACT

An abrasive dentifrice composition which effects enhanced antiplaque and breath freshening properties which comprises an orally acceptable vehicle containing a combination of a safe and effective amount of an antibacterial agent and at least two enzyme ingredients.

10 Claims, No Drawings

ANTIBACTERIAL DENTIFRICE EXHIBITING ENHANCED ANTIPLAQUE AND BREATH FRESHENING PROPERTIES

BACKGROUND OF THE INVENTION

1. Field of the Invention

The present invention relates to an oral care composition which contains a cationic antibacterial compound which composition is effective in retarding bacterial plaque accumulation on teeth and more particularly to a dentifrice composition containing a cationic antibacterial compound and a proteolytic enzyme which achieves plaque reduction with superior breath freshening characteristics.

2. The Prior Art

Halitosis, the technical term for bad breath, or Fetor ex Otis, is an undesirable condition. As a matter of fact, everyone, excluding the very young, occasionally has bad breath, with approximately 25% suffering on a regular basis and the problem tends to get worse and more frequent as one gets older. The problem seems to be evenly split between men and women. Bad breath results when proteins from the food we eat and saliva debris are broken down by bacteria. Even the cleanest mouth hosts millions of bacteria which have the potential to decompose these protein-containing particles left in the mouth. The tongue, with its fissures and large, bumpy surface area, retains considerable quantities of food and debris that support and protect a large bacterial population. Under low oxygen condition, this bacterial population forms foul smelling products, called volatile sulfur compounds (VSC)—such as hydrogen sulfide ("rotten eggs") and methyl mercaptans ("skunk smell") and other odorous and bad tasting compounds. Up to 80-90% of bad breath that originates in the mouth is by this mechanism.

Dental plaque or plaque bio-film is a soft deposit that forms on teeth and is comprised of an accumulation of bacteria and salivary as well as food by-products. Plaque adheres tenaciously at the points of irregularity or discontinuity, e.g., on rough calculus surfaces, at the gum line, on tongue surface and within crevices, and the like. Besides being unsightly, plaque is implicated in the occurrence of gingivitis and other forms of periodontal disease.

Bacteria thrive on the tongue. For the most part, the bacteria are a part of a protective bio-film that essentially renders them resistant to most treatments. Few people clean their tongue after brushing, even though it's been shown that as much as 50 percent of the mouth's bacteria can be found here. Additionally, for many people, brushing or scraping the tongue is difficult because of the gag reflex. Therefore, cleaning the tongue non-mechanically is highly desirable for those who are unable to do so with a mechanical device.

A wide variety of antibacterial agents have been suggested in the art to retard plaque formation and the oral infections and dental disease associated with plaque formation. For example, cationic antibacterial compounds such as cetyl pyridinium chloride are well known to the art for their antibacterial activity and have been used in oral compositions to counter plaque formation by bacterial accumulation in the oral cavity.

In spite of the extensive prior art relating to antibacterial dentifrice compositions, there is still a need in the art to formulate a dentifrice product capable of delivering an antibacterial agent having enhanced effect in the retardation of bacterial plaque accumulation on teeth, as well as on the tongue, without inhibiting the bioavailability of the antibacterial compound. The delivery of the antibacterial compound to the tongue will allow for effective control of bad breath.

SUMMARY OF THE INVENTION

The present invention encompasses a dental composition containing in an orally acceptable vehicle a combination of an antibacterial compound, and a proteolytic enzyme whereby superior reduction of plaque accumulation is accompanied by enhanced malodor reduction.

DESCRIPTION OF THE PREFERRED EMBODIMENTS

In the practice of the present invention the dental composition containing the antibacterial agent and enzyme ingredients is formulated as a paste using a vehicle containing a safe and effective amount of the antibacterial and enzyme compounds.

Cationic antibacterial agents useful in the practice of the present invention are well known in the art and include both nonionic and cationic agents. See, for instance the section on "Quaternary Ammonium and Related Compounds" in the article on "Antiseptics and Disinfectants" in Kirk-Othmer Encyclopedia of Chemical Technology, $2^{nd}$ edition (vol. 2, pp. 632-635), incorporated herein by reference. Cationic antibacterial compounds which possess antibacterial activity (i.e., are germicides) are used against bacteria and have been used in oral compositions to counter plaque formation caused by bacteria in the oral cavity.

Among the most common of these cationic antibacterial antiplaque quaternary ammonium compounds is benzethonium chloride, or diisobutylphenoxyethoxyethyl dimethyl benzyl ammonium chloride, and cetyl pyridinium chloride. In a dentifrice preparation this material is highly effective in promoting oral hygiene by reducing the formation of dental plaque and calculus, which is generally accompanied by a reduction in periodontal diseases.

Other cationic antibacterial quaternary ammonium compounds useful in the practice of the present invention include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, benzyl dimethyl stearyl ammonium chloride, cetyl pyridinium chloride (CPC) and quaternized 5-amino-1,3-bis(2-ethylhexyl)-5-methyl hexa hydro-pyrimidine are typical quaternary ammonium antibacterial agents.

The antibacterial agent is included in the dentifrice at a concentration of about 0.10 to about 1.5% by weight and preferably about 0.3 to about 1.2% by weight.

Abrasives

Abrasives preferred for use the practice of the present invention include silica materials and particularly silica gels and precipitated amorphous silica having an oil absorption value of less than 100 cc/100 g silica and preferably in the range of from about 45 cc/100 g to less than about 70 cc/100 g silica. These silicas are colloidal particles having an average particle size ranging from about 3 microns to about 12 microns, and more preferably between about 5 to about 10 microns and a pH range from 4 to 10 preferably 6 to 9 when measured as a 5% by weight slurry.

Oil absorption values are measured using the ASTM Rub-Out Method D281. The low oil absorption silica abrasive is present in the oral are compositions of the present invention at a concentration of about 5 to about 40% by weight and preferably about 10 to about 30% by weight.

Low oil absorption silica abrasives particularly useful in the practice of the present invention are marketed under the trade designation Sylodent XWA by Davison Chemical Division of W.R. Grace & Co., Baltimore, Md. 21203. Sylodent 650 XWA, a silica hydrogel composed of particles of colloidal silica having a water content of 29% by weight averaging from about 7 to about 10 microns in diameter, and an oil absorption of less than 70 cc/100 g of silica is a preferred example of a low oil absorption silica abrasive useful in the practice of the present invention.

Another low oil absorption silica abrasive particularly useful in the practice of the present invention is marketed under the trade designation DP-105 by J.M. Huber Chemicals Division, Havre de Grace, Md. 21078 is a precipitated amorphous silica having an average particle size distribution from 5 to 12 microns and an oil absorption in the range of 50 to 70 cc/100 g.

Other abrasives which may be used in the practice of the present invention include precipitated silicas having a mean particle size of up to about 20 microns, such as Zeodent 115, marketed by J.M. Huber Chemicals Division, Havre de Grace, Md. 21078, or Sylodent 783 marketed by Davison Chemical Division of W.R. Grace & Company, sodium metaphosphate, potassium metaphosphate, tricalcium phosphate, dihydrated dicalcium phosphate, aluminum silicate, calcined alumina, bentonite or other siliceous materials, or combinations thereof.

The abrasive materials may be used individually as the sole abrasive in preparing the dental composition of the present invention or in combination with other known dentifrice abrasives. The total quantity of abrasive present in the dentifrice compositions of the present invention is at a level of from about 5% to about 60% by weight, preferably from about 10% to about 55% by weight when the dentifrice composition is a toothpaste.

Enzymes

The enzymes useful in the practice of the present invention include protein substances within the class of proteases, which breakdown or hydrolyze proteins (proteases). These proteolytic enzymes are obtained from natural sources or by the action of microorganisms having a nitrogen source and a carbon source. Examples of proteolylic enzymes useful in the practice of the present invention include papain, bromelain, chymotrypsin, ficin and alcalase.

Papain obtained from the milky latex of the Papaya tree is the proteolytic enzyme preferred for use in the practice of the present invention and is incorporated in the oral care composition of the present invention in an amount of about 0.1 to about 10% by weight and preferably about 0.5 to about 5% by weight, such papain having an activity of 150 to 300 MCU per milligram as determined by the Milk Clot Assay Test of the Biddle Sawyer Group (see J. Biol. Chem., vol. 121, pages 737-745).

An additional enzyme which may be formulated in combination with a protease enzyme such as papain is glucoamylase. Glucoamylase is a saccharifying glucoamylase of *Aspergillus niger* origin cultivated by fermentation. This enzyme can hydrolyze both the alpha-D-1,6 glucosidic branch points and the alpha-1,4 glucosidic bonds of glucosyl oligosaccharides. The product of this invention comprises about 0.001 to 2% of the carbohydrase and preferably about 0.01 to 0.55% by weight. Additional carbohydrases useful in accordance with this invention are glucoamylase, alpha and beta-amylase, dextranase and mutanase.

Other enzymes which may be used in the practice of the present invention include other carbohydrases such as alpha-amylase, beta-amylase, dextranase and mutanase and lipases such as plant lipase, gastric lipase, pancreatic lipase, pectinase, tannase lysozyme and serine proteases.

The lipase enzyme is derived from a select strain of *Aspergillus niger*, exhibiting random cleaving of the 1,3 positions of fats and oils. The enzyme has maximum lipolytic activity at pH 5.0 to 7.0 when assayed with olive oil. The enzyme has a measured activity of 120,000 lipase units per gram. The lipase may be included in the dentifrice composition at a concentration of about 0.010 to about 5.0% by weight and preferably about 0.02 to about 0.10% by weight.

The presence of tannase enzyme can be further beneficial in facilitating the breakdown of extrinsic stain. Tannase enzymes have been purified from *Aspergillus niger* and *Aspergillus allianceus* and are useful in the hydrolysis of tannins, known to discolor the tooth surface.

Other suitable enzymes which can comprise the present invention include lysozyme, derived from egg white, which contains a single polypeptide chain crosslinked by four disulfide bonds having a molecular weight of 14,600 daltons. The enzyme can exhibit antibacterial properties by facilitating the hydrolysis of bacterial cell walls cleaving the glycosidic bond between carbon number 1 of N-acetylmuramic acid and carbon number 4 of N-acetyl-D-glucosamine, which in vivo, these two carbohydrates are polymerized to form the cell wall polysaccharide. Additionally, pectinase, an enzyme that is present in most plants facilitates the hydrolysis of the polysaccharide pectin into sugars and galacturonic acid.

Dentifrice Vehicle

The orally-acceptable dentifrice vehicle used to prepare the dentifrice composition comprises a water-phase, containing a humectant therein. The humectant is preferably glycerin, sorbitol, xylitol, and/or propylene glycol of molecular weight in the range of 200 to 1,000; but, other humectants and mixtures thereof may also be employed. The humectant concentration typically totals about 5 to about 70% by weight of the oral composition.

Reference hereto to sorbitol refers to the material typically commercially available as a 70% aqueous solution. Water is present typically in amount of at least about 10% by weight, and generally about 15 to 30% by weight of the oral composition. Water employed in the preparation of commercially suitable toothpastes should preferably be deionized and free of organic impurities. These amounts of water include the free water which is added plus that which is introduced with other materials such as with sorbitol.

The dentifrice compositions of the present invention can contain a variety of optional dentifrice ingredients. As described below, such optional ingredients can include, but are not limited to, thickening agents, surfactants, a source of fluoride ions, a synthetic anionic polycarboxylate, a flavoring agent, antitartar and coloring agents.

Thickening Agents

Thickeners used in the compositions of the present invention include natural and synthetic gums and colloids. Not all naturally occurring polymer thickeners (such as cellulose or carrageenans) are compatible with dentifrice ingredients (specifically enzymes) of dentifrice compositions when formulated in the presence of proteolytic enzymes. Thickeners compatible with proteolytic enzymes include xanthan gum, polyglycols of varying molecular weights sold under the tradename Polyox, and polyvinylpyrrolidone. Compatible inorganic thickeners include amorphous silica compounds which function as thickening agents and include colloidal silicas compounds available under the trade designation Cab-o-sil manufactured by Cabot Corporation and distributed by Lenape Chemical, Bound Brook, N.J.; Zeodent 165 from J.M. Huber Chemicals Division, Havre de Grace, Md. 21078;

and Sylodent 15, available from Davison Chemical Division of W.R. Grace Corporation, Baltimore, Md. 21203. Other inorganic thickeners include natural and synthetic clays, lithium magnesium silicate (laponite) and magnesium aluminum silicate (Veegum).

The thickening agent is present in the dentifrice composition in amounts of about 0.1 to about 10% by weight, preferably about 0.5 to about 4.0% by weight.

Surfactants

Surfactants are used in the compositions of the present invention to achieve increased prophylactic action and render the dentifrice compositions more cosmetically acceptable. The surfactant is preferably a detersive material which imparts to the composition detersive and foaming properties.

Anionic surfactants such as higher alkyl sulfates such as sodium lauryl sulfate are not compatible with enzymes. Anionic surfactants facilitate denaturing of the enzyme and loss in activity. As a result, it is important to the practice of the present invention to use a surfactant or combination of surfactants that are compatible with the enzymes present in the toothpaste formulation and provide the requisite foaming characteristics. Examples of enzyme compatible surfactants include nonanionic polyoxyethylene surfactants such as Polyoxamer 407, Steareth 30, Polysorbate 20, and amphoteric surfactants such as cocamidopropyl betaine and cocamidopropyl betaine lauryl glucoside. Preferred surfactants include a combination of Pluronic F127, Polyoxamer 407, Polysorbate 20, and cocamidopropyl betaine at a total surfactant concentration in the dentifrice composition of between about 2 to about 10% by weight and preferably between about 3.5 to about 6.5% by weight at weight ratios of 2.5 Polyaxomer 407, 3.3 Polysorbate-20 and 1.0 cocamidopropyl betaine.

Fluoride

The dentifrice composition of the present invention may also contain a source of fluoride ions or fluorine-providing component, as anticaries agent in amount sufficient to supply about 25 ppm to 5,000 ppm of fluoride ions and include inorganic fluoride salts, such as soluble alkali metal salts. For example, preferred fluoride sources which are compatible with enzymes present in the composition are sodium fluoride, potassium fluoride, sodium fluorosilicate, ammonium fluorosilicate, as well as tin fluorides, such as stannous fluoride and stannous chloride. Sodium fluoride is preferred.

Antitartar Agents

In addition to fluoride compounds, there may also be included antitartar agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$ long chain polyphosphates such as sodium hexametaphosphate and cyclic phosphates such as sodium trimetaphosphate. These antitartar agents are included in the dentifrice composition at a concentration of about 1 to about 5% by weight.

Enzyme Stabilizing Agents

The dentifrice composition of the present invention may also contain ingredients which stabilize enzymes in a dentifrice environment. These stabilizers protect the enzyme from inactivation by chelating metal impurities present in the dentifrice composition which have the propensity to denature the active site of the enzyme by protecting the enzyme from oxidation. Chelating agents include, ethylene diamine tetraacetic acid (EDTA) and sodium gluconate at concentrations between 0.01 and 1%, preferably between 0.1 and 0.5%. Agents stabilizing the enzyme against oxidation include sodium bisulfite, metal gallates, sodium stannate and ascorbic acid at concentrations between about 0.03 and about 2.0%, preferably between about 0.1 and about 0.75%.

Anionic Polycarboxylate

Synthetic anionic polycarboxylates may also be used in the dentifrice compositions of the present invention as an efficacy enhancing agent for any antibacterial, antitartar or other active agent within the dentifrice composition. Such anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methylvinylether/maleic anhydride having a molecular weight (M.W.) of about 30,000 to about 1,800,000 most preferably about 30,000 to about 700,000. Examples of these copolymers are available from GAF Corporation under the tradename Gantrez, e.g. AN 139 (M.W. 500,000), AN 119 (M.W. 250,000); S-97 Pharmaceutical Grade (M.W. 700,000), AN 169 (M.W. 1,200,000-1,800,000), and AN 179 (M.W. above 1,800,000); wherein the preferred copolymer is S-97 Pharmaceutical Grade (M.W. 700,000).

When present, the anionic polycarboxylate is employed in amounts effective to achieve the desired enhancement of the efficacy of any antibacterial, antitartar or other active agent within the dentifrice composition. Generally, the anionic polycarboxylates is present within the dentifrice composition from about 0.05% to about 4% by weight, preferably from about 0.5% to about 2.5% by weight.

Flavor

The dentifrice composition of the present invention may also contain a flavoring agent. Flavoring agents which are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, majoram, cinnamon, lemon, lime, grapefruit, and orange. Also useful are such chemicals as menthol, carvone, and anethole. Of these, the most commonly employed are the oils of peppermint and spearmint.

The flavoring agent is incorporated in the dentifrice composition at a concentration of about 0.1 to about 5% by weight and preferably about 0.5 to about 1.5% by weight.

Other Ingredients

Various other materials may be incorporated in the dentifrice compositions of this invention, including desensitizers, such as potassium nitrate; whitening agents; preservatives; silicones; and chlorophyll compounds. These additives, when present, are incorporated in the dentifrice composition in amounts which do not substantially adversely affect the properties and characteristics desired.

Preparation of the Dentifrice

The preparation of dentifrices is well known in the art. More specifically, to prepare a dentifrice of the present invention, generally the humectants e.g. glycerin, sorbitol, propylene glycol, and polyethylene glycol; are dispersed in the water in a conventional mixer under agitation. Into the dispersion are added the enzyme or enzymes organic thickeners, such as xanthan gum; any anionic polycarboxylate; any salts, such as sodium fluoride anticaries agents; tetrasodium pyrophosphate, sodium tripolyphosphate anticalculus salts and any sweeteners; the resultant mixture is agitated until a homogeneous gel phase is formed. Into the gel phase are added a pigment such as $TiO_2$, and any acid or base required to adjust the pH. These ingredients are mixed until a homogenous phase is obtained. The mixture is then transferred to a high speed/vacuum mixer; wherein, the inorganic silica thickener, such as Zeodent 165; and surfactant ingredients are added to the mixture. The low oil absorption silica abrasive is added at this point, along with other abrasives to be used in the composition. The mixture is then mixed at high speed for from 5 to 30 minutes, under vacuum of from about 20 to 50 mm of Hg, preferably about 30 mm Hg. The resultant product is in each case a homogeneous, semi-solid, extrudable paste or gel product.

The following example further describes and demonstrates preferred embodiments within the scope of the present invention. The example is given solely for illustration, and are not to be construed as limitation of this invention as many variations thereof are possible without departing from its spirit and scope.

EXAMPLE 1

Toothpaste compositions containing CPC and a mixture of enzymes were prepared having the following ingredients:

| INGREDIENT* | COMPOSITION NUMBER | | | | |
|---|---|---|---|---|---|
| | 1 | 2 | C1 | C2 | C3 |
| Deionized water | 16.0 | 14.0 | 16.0 | 14.0 | 16.0 |
| Pluronic F127 | 1.5 | 1.5 | 1.5 | 1.5 | 1.5 |
| Sodium MFP | 0.76 | 0.76 | 0.76 | 0.76 | 0.76 |
| Sodium saccharin | 0.40 | 0.40 | 0.40 | 0.40 | 0.40 |
| Sorbitol (70%) | 18.305 | 7.0 | 18.805 | 7.0 | 18.61 |
| Glycerin | 20.00 | 16.565 | 20.00 | 16.87 | 20.00 |
| Sodium tripolyphosphate | 3.00 | — | 3.00 | — | 3.00 |
| Xanthan | 0.55 | 0.60 | 0.55 | 0.60 | 0.55 |
| Laponite D (polymer) | 0.70 | 0.7 | 0.70 | 0.7 | 0.70 |
| Zeodent-115 | 5.00 | — | 5.00 | — | 5.00 |
| Zeodent-165 | 2.00 | — | 2.00 | — | 2.00 |
| Sylodent XWA650 | 20.00 | — | 20.00 | — | 20.00 |
| Dicalcium phosphate | — | 50.0 | — | 50.0 | — |
| Flavor | 1.10 | 1.10 | 1.10 | 1.10 | 1.10 |
| Tetrasodium pyrophosphate | 2.00 | 0.5 | 2.00 | 0.5 | 2.00 |
| Titanium dioxide | 0.4 | 0.4 | 0.4 | 0.4 | 0.4 |
| Tegobetaine | 2.00 | 0.200 | 2.00 | 0.200 | 2.00 |
| Polysorbate 20 | 2.00 | 2.00 | 2.00 | 2.00 | 2.00 |
| PEG 600 | 3.00 | 3.00 | 3.00 | 3.00 | 3.00 |
| Papain | 0.205 | 0.205 | 0.205 | — | — |
| Glucoamylase | 0.10 | 0.10 | 0.10 | — | — |
| Sodium bisulfite | 0.10 | 0.10 | 0.10 | 0.10 | 0.10 |
| Sodium phosphate monobasic | 0.03 | 0.03 | 0.03 | 0.03 | 0.03 |
| Anhy. Na Phosphate dibasic | 0.20 | 0.20 | 0.20 | 0.20 | 0.20 |
| Polyox | 0.15 | 0.15 | 0.15 | 0.15 | 0.15 |
| Cetylpyridinium chloride | 0.50 | 0.50 | — | 0.50 | 0.50 |
| TOTAL | 100 | 100 | 100 | 100 | 100 |

*Weight %

MIC Assay

The compositions listed in Table I were tested using a microbiological assay namely, Minimum Inhibitory Concentration (MIC).

Gram-positive oral bacterium *Actinomyces viscosus* was routinely grown overnight in trypticase soy broth (Difco Labs, Detroit, Mich.) at 37° C. A gram stain of the cultures was prepared to determine the purity of the cultures prior to in vitro testing of the rinse compositions. The bacterial strain grown for 18 hours at 37° C. in trypticase soy broth (TSB) was diluted in fresh broth to adjust its optical density between 0.1 and 0.2 absorption units at 610 nm prior to MIC determinations.

The MIC of Compositions 1 and 2 diluted in TSB and was determined using the microtiter format according to standard procedures (Manual of Clinical Microbiology, 1995). The MIC value after 8 weeks exposure was less than one ppm for both Compositions 1 and 2. Neat CPC also had an MIC value of less than one ppm after 8 weeks of exposure.

EXAMPLE II

For purposes of comparison the procedure of Example I was repeated except that one composition (Composition C1) was prepared similar to Composition 1 except CPC was not included in the composition. A second composition (Composition C2) was prepared similar to Composition 2 except no enzymes were included in the composition. For purposes of further comparison, a third composition (Composition C3), similar to Composition 1 was prepared which did not contain enzymes. A placebo composition which was a conventional silica based dentifrice system containing 0.24% NaF was also evaluated.

All compositions were tested for their ability to reduce tongue microflora, especially those species responsible for the generation of $H_2S$. Patients swabbed the back of the tongue for bacterial collection at baseline and four hours post treatment. These samples were plated onto lead acetate agar media for the selection of $H_2S$-forming bacteria and incubated anaerobically. After 72 hours, colony-forming units of $H_2S$-forming bacteria were enumerated. The mean colony forming unit results were used to calculate percent reduction from baseline.

Table II represents in-vivo tongue microflora study with bacterial sampling at baseline and at four hours post-brushing with Compositions 1 and 2 which exhibit a 76-82% reduction in bacteria responsible for oral malodor compared to a 52% and 47% reduction for (Composition C1) either enzymes or CPC alone. In addition, a combination of Compositions 1 and 2 substantially reduced tongue bacteria compared to placebo in both abrasive systems providing improved efficacy without compromising the efficacy of the actives.

TABLE II

Reduction of malodor tongue bacteria 4 hours post treatment.

| Composition | Baseline Mean CFU* | After 4 hours Mean CFU | % Reduction of Malodor Bacteria |
|---|---|---|---|
| 1 | $1.9\ 10^5$ | $3.9\ 10^4$ | 80 |
| 2 | $1.2\ 10^5$ | $1.4\ 10^4$ | 88 |
| C1 | $1.7\ 10^5$ | $6.8\ 10^4$ | 60 |
| C2 | $1.1\ 10^5$ | $7.1\ 10^4$ | 35 |
| C3 | $1.2\ 10^5$ | $6.4\ 10^4$ | 46 |
| Placebo | $1.0\ 10^5$ | $9.2\ 10^4$ | 9 |

CFU = Colny forming units

EXAMPLE III

The dentifrice compositions of the present invention were also found to control breath VSC formation in a pilot breath VSC clinical study involving patients. VSC levels were measured using a Halimeter™. (Model #RH17E), a commercially available sulfide monitor using a breath sample drawn from the subject's mouth through a straw directly into the sample port detector. A VSC level above 190 ppb is considered as offensive mouth odor. Breath-odor was measured using a Halimeter at baseline and at four hours after brushing the teeth for one minute and swishing the slurry for 30 seconds. The results in Table III are consistent with data represented in Table II indicating 'a greater reduction in breath VSC's responsible for oral malodor when compared to comparative compositions in which enzymes were not used in combination with CPC.

TABLE III

| Composition | Baseline Avg [VSC] in ppb* | After 4 hours Avg [VSC] in ppb | % Reduction of Oral Malodor |
|---|---|---|---|
| 1 | 460 | 160 | 65 |
| C1 | 290 | 150 | 47 |
| C2 | 250 | 140 | 42 |
| C3 | 290 | 140 | 49 |
| Placebo | 300 | 210 | 30 |

*ppb = parts per billion

What is claimed is:

1. A dentifrice composition which effects enhanced antiplaque and breath malodor reduction comprising:
an orally acceptable vehicle;
a silica abrasive,
from about 0.1 to about 5%, by weight, of papain;
a quaternary ammonium compound; and
glucoamylase.

2. The composition of claim 1 wherein the silica abrasive is present in the composition at a concentration of about 5 to about 40% by weight of the composition.

3. The composition of claim 1 further comprising dicalcium phosphate.

4. The composition of claim 3 wherein the dicalcium phosphate is present in the composition at a concentration of about 5 to about 60% by weight.

5. A method for effecting enhanced antiplaque and breath malodor reduction comprising applying the composition of claim 1 to an oral cavity surface.

6. The method of claim 5 wherein the silica abrasive is present in the dentifrice at a concentration of about 5 to about 40% by weight of the composition.

7. The composition of claim 1, wherein the silica has an oil absorption value of from 50 cc/100 g to less than about 70 cc/100 g.

8. The method of claim 5, wherein the silica has an oil absorption value of from 50 cc/100 g to less than about 70 cc/100 g.

9. The method of claim 5, further comprising dicalcium phosphate.

10. The method of claim 9, wherein the dicalcium phosphate is present in the composition at a concentration of about 5 to about 60% by weight.

* * * * *